United States Patent
Wang et al.

(10) Patent No.: US 10,633,703 B2
(45) Date of Patent: Apr. 28, 2020

(54) METHODS AND SYSTEMS FOR PREDICTING THE RISK OF TRANSGENE SILENCING

(71) Applicant: Dow AgroSciences LLC, Indianapolis, IN (US)

(72) Inventors: Pohao Wang, Carmel, IN (US); Shreedharan Sriram, Indianapolis, IN (US); Lakshmi Sastry-Dent, Avon, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 679 days.

(21) Appl. No.: 15/333,574

(22) Filed: Oct. 25, 2016

(65) Prior Publication Data

US 2017/0130266 A1      May 11, 2017

Related U.S. Application Data

(60) Provisional application No. 62/253,213, filed on Nov. 10, 2015.

(51) Int. Cl.
| | |
|---|---|
| *C12Q 1/6876* | (2018.01) |
| *G16B 25/00* | (2019.01) |
| *C12Q 1/6895* | (2018.01) |
| *C12N 15/82* | (2006.01) |
| *G16B 20/00* | (2019.01) |

(52) U.S. Cl.
CPC ........... *C12Q 1/6876* (2013.01); *C12N 15/82* (2013.01); *C12Q 1/6895* (2013.01); *G16B 20/00* (2019.02); *G16B 25/00* (2019.02); *C12Q 2600/154* (2013.01); *C12Q 2600/158* (2013.01)

(58) Field of Classification Search
None
See application file for complete search history.

(56) References Cited

U.S. PATENT DOCUMENTS

2009/0143240 A1    6/2009    Harbison

FOREIGN PATENT DOCUMENTS

| WO | WO2013/119770 | 8/2013 |
| WO | WO2014/039330 | 3/2014 |

OTHER PUBLICATIONS

Edwards et al. Plant genome sequencing: applications for crop improvement Plant Biotechnology Journal vol. 8, pp. 2-9 (Year: 2010).*
Furey et al. ChIP-seq and beyond: new and improved methodologies to detect and characterize protein-DNA interactions Nature Reviews Genetics vol. 13, pp. 840-852 (Year: 2012).*
Ayyappan, et al. Genome-Wide Profiling of Histone Modifications (H3K9me2 and H4K12ac) and Gene Expression in Ruse (Uromyces appendicuiatus) Inoculated Common Bean (*Phaseolus vulgaris* L.). PLoS One. Jul. 13, 2015, vol. 10, pp. 1-29, abstract; p. 4, second paragraph; p. 22, first paragraph; DOI:10.1371/journal.pono.0132176.
Charron, et al. Dynamic Landscapes of Four Histone Modifications During Deetiolation in *ArabidopsIs*. The Plant Cell. Dec. 2009, vol. 21, pp. 3742-3748, abstract; p. 3742, second column, second paragraph; D0I:10.1105/tpc.109.066845.
International Search Report dated Jan. 19, 2017 for PCT/US2016/058633.
Written Opinion dated Jan. 19, 2017 for PCT/US2016/058633.
International Preliminary Report on Patentability dated May 15, 2018 for PCT/US2016/058633.
European Search Report dated May 31, 2019 for Application No. 16864761.8-1126 / 3374907 of PCT/US2016/058633.
De La Fuente, Lorena, et al. "Genome-wide changes in histone H3 lysine 27 trimethylation associated with bud dormancy release in peach." Tree Genetics & Genomes 11.3 (2015): 45.
He, Guangming, et al. "Global epigenetic and transcriptional trends among two rice subspecies and their reciprocal hybrids." The Plant Cell 22.1 (2010): 17-33.
Mutsov, Vesco, and Gary Felsenfeld. "Silencing of transgene transcription precedes methylation of promoter DNA and histone H3 lysine 9." The EMBO journal 23.1 (2004): 138-149.
Karlic, Rosa, et al. "Histone modification levels are predictive for gene expression." Proceedings of the National Academy of Sciences 107.7 (2010): 2926-2931.
Feng, J., et al. "Identifying ChIP-seq enrichment using MACS." Nature protocols 7.9 (2012): 1728.

* cited by examiner

Primary Examiner — John S Brusca (57) ABSTRACT

The present invention is based on the use of the H3K9me2 methylation levels in plant genomes to predict transgene silencing, transgene stability, and/or transgene expression level. Provided are methods and/or systems for generating whole-genome H3K9me2 maps and its use with an assigned threshold value for predicting gene silencing. The methods and/or systems provided herein can be used in high-throughput setting for screening large number of transformed event in a relatively short period of time as compared to existing technologies.

7 Claims, 1 Drawing Sheet

METHODS AND SYSTEMS FOR PREDICTING THE RISK OF TRANSGENE SILENCING

CROSS REFERENCE TO RELATED APPLICATIONS

This application claims priority under 35 U.S.C. § 119 of U.S. Provisional Patent Application Ser. No. 62/253,213, filed Nov. 10, 2015, which is hereby incorporated by reference in its entirety.

BACKGROUND OF THE INVENTION

The genome of plants, for example soybean or maize plants, was successfully transformed with transgenes in the 1990's. Over the last twenty years, numerous methodologies have been developed for transforming the genome of plants, wherein a transgene is stably integrated into the genome of plants. The evolution of plant transformation methodologies has resulted in the capability to successfully introduce a transgene comprising an agronomic trait within the genome of plants. The introduction of insect resistance and herbicide tolerant traits within plants provided producers with a new and convenient technological innovation for controlling insects and a wide spectrum of weeds, which was unparalleled in cultivation farming methods.

Current transformation methodologies rely upon the random insertion of transgenes within the genome of plants. Because transgenic events may randomly integrate within gene transcriptional sequences, such events may interrupt the expression of endogenous traits and alter the growth and development of the plant. In addition, the transgenic events may indiscriminately integrate into locations of the genome that are susceptible to gene silencing, culminating in the reduced or complete inhibition of transgene expression either in the first or subsequent generations of transgenic plants. Finally, the random integration of transgenes within the plant genome requires considerable effort and cost in identifying the location of the transgenic event and selecting transgenic events that perform as designed without agronomic impact to the plant.

Therefore, there is the need for inventions that are useful to evaluate the effectiveness of the integration sites of transgene for gene expression, and/or to predict the risk for transgene silencing.

SUMMARY OF THE INVENTION

This invention is related to methods and systems for predicting the risk of transgene silencing, and/or predicting expression levels of transgenes, and/or predicting stability and/or effectiveness of transgene integration sites. In one aspect, provided is a method for predicting the risk of transgene silencing. The method comprises:
(a) generating histone methylation/acetylation profile data in a plant's genome;
(b) assemble the histone methylation/acetylation profile data of step (a) into a histone methylation/acetylation database showing peak numbers of the histone methylation/acetylation profiles;
(c) analyzing sequences of at least one transgene insertion site; and
(d) comparing the sequences of the transgene insertion site of step (c) with the histone methylation/acetylation database of step (b);

wherein (i) if the transgene insertion site falls into peak zero or peak one of the methylation/acetylation profiles, there is no risk of transgene silencing, or
(ii) if the transgene insertion site falls into peak two or more of the histone methylation/acetylation profiles, there is significant risk of transgene silencing.

In one embodiment, the histone methylation/acetylation profile data is generated using a chromatin immunoprecipitation sequencing (ChIP-seq) assay. In another embodiment, the histone methylation/acetylation profile data is associated with histone methylation/acetylation selected from the group consisting of H3K4me2, H3K4me3, H3K9/14ac, H3K9me2, H3K9me3, H3K27me1, H3K27me3 and H4K20me3, and combinations thereof. In another embodiment, the histone methylation/acetylation profile data is associated with histone methylation/acetylation selected from the group consisting of H3K9me2, H3K9me3, H3K27me1, H3K27me3 and H4K20me3, and combinations thereof. In another embodiment, the histone methylation/acetylation profile data is associated with H3K9me2 methylation. In another embodiment, the plant is selected from soybean, maize, canola, cotton, wheat, and rice. In another embodiment, the sequences of the transgene insertion site are obtained by direct sequencing.

In another aspect, provided is computerized system for predicting the risk of transgene silencing. The system comprises:
(a) a histone methylation/acetylation database showing peak numbers of the histone methylation/acetylation profiles in a plant's genome;
(b) an input module where an user inputs sequences of at least one transgene insertion site; and
(c) an output module shows prediction of the risk of transgene silencing, wherein the prediction is based on comparison of the inputted sequences of Step (b) and the histone methylation/acetylation profiles of Step (a).

In one embodiment, the histone methylation/acetylation profile data is generated using a chromatin immunoprecipitation sequencing (ChIP-seq) assay. In another embodiment, the histone methylation/acetylation profile data is associated with histone methylation/acetylation selected from the group consisting of H3K4me2, H3K4me3, H3K9/14ac, H3K9me2, H3K9me3, H3K27me1, H3K27me3 and H4K20me3, and combinations thereof. In another embodiment, the histone methylation/acetylation profile data is associated with histone methylation/acetylation selected from the group consisting of H3K9me2, H3K9me3, H3K27me1, H3K27me3 and H4K20me3, and combinations thereof. In another embodiment, the histone methylation/acetylation profile data is associated with H3K9me2 methylation. In another embodiment, the plant is selected from soybean, maize, canola, cotton, wheat, and rice. In another embodiment, the sequences of the transgene insertion site are obtained by direct sequencing.

In another aspect, provided is a process for use in a computerized system for predicting the risk of transgene silencing. The process comprises:
(a) inputting sequences of at least one transgene insertion site into the system provided herein by an user; and
(b) receiving output from the system provided herein for prediction of the risk of transgene silencing, wherein the prediction is based on comparison of the inputted sequences of the transgene insertion site and the histone methylation/acetylation profiles within the system.

DETAILED DESCRIPTION OF THE INVENTION

The present invention is based on the use of the H3K9me2 methylation levels in plant genomes to predict transgene silencing, transgene stability, and/or transgene expression level. Provided are methods and/or systems for generating whole-genome H3K9me2 maps and its use with an assigned threshold value for predicting gene silencing. The methods and/or systems provided herein can be used in high-throughput setting for screening large number of transformed event in a relatively short period of time as compared to existing technologies.

Transgene performance and heritable transgene stability are important for the success of trait product concepts. Several approaches have been used in the past to assess transgene expression and performance including quantitative expression analyses techniques including for example RT-PCR, DNA methylation, and transgenerational stability testing. These approaches take time and resources during the trait development process and require multiple generations of tracking transgenic events and could potentially lead to picking bad transgenic events to promote for downstream product development.

Epigenetic marks refer to enzyme-mediated chemical modifications of DNA and of its associated chromatin proteins. Typically epigenetic marks do not alter the primary sequence of DNA, but they are important in regulating genome function. DNA modifications (including cytosine methylation, posttranslational modifications of histone tails and the histone core, and the positioning of nucleosomes), may influence the transcriptional state and other functional aspects of chromatin. Histone modifications are a cellular system involving transcriptional regulatory mechanisms. Both activating type (for example H3K4me3 and H3K9/14ac) and repressive type (for example H3K27me3, H3K9me3, H3K9me2, and H4K20me3) histone marks have been previously identified. In particular di-methylation of a specific lysine (K9) in the histone H3, commonly known as H3K9me2, has been characterized as an epigenetic mark indicating closed chromatin or transcriptional repression at a genome scale. Provided are methods and systems for the use of H3K9me2 as a diagnostic tool to understand the chromatin state of the genomic location around an integrated transgene and predict the potential risk of gene silencing in transgenic events. The applicability of the methods and systems provided include for example event sorting or selection in the trait development process. Specifically, data for genome-wide H3K9me2 profiling in Soybean roots and shoots are provided as an example. In some embodiment, H3K9me2 methylation level at the locus of a transgene insertion site can be used to identify/predict events with a higher probability of stable expression.

In some embodiment, whole-genome H3K9me2 maps are generated for each crop plant. In some embodiment, a database is generated according to such whole-genome H3K9me2 maps. In some embodiment, such database can be used to predict the chromatin structure within the locus of our interest according to the methods and/or systems provided.

Unless otherwise indicated, all technical and scientific terms used herein have the same meaning as they would to one skilled in the art of the present invention. Practitioners are particularly directed to Sambrook et al. Molecular Cloning: A Laboratory Manual (Second Edition), Cold Spring Harbor Press, Plainview, N.Y., 1989, and Ausubel F M et al. Current Protocols in Molecular Biology, John Wiley & Sons, New York, N.Y., 1993, for definitions and terms of the art. It is to be understood that this invention is not limited to the particular methodology, protocols, and reagents described, as these may vary.

As used herein, the phrase "about" refers to greater or lesser than the value or range of values stated by 10 percent, but is not intended to designate any value or range of values to only this broader definition. Each value or range of values preceded by the term "about" is also intended to encompass the embodiment of the stated absolute value or range of values As used herein, the phrase "vector" refers to a piece of DNA, typically double-stranded, which can have inserted into it a piece of foreign DNA. The vector can be for example, of plasmid or viral origin, which typically encodes a selectable or screenable marker or transgenes. The vector is used to transport the foreign or heterologous DNA into a suitable host cell. Once in the host cell, the vector can replicate independently of or coincidental with the host chromosomal DNA. Alternatively, the vector can target insertion of the foreign or heterologous DNA into a host chromosome.

As used herein, the phrase "transgene vector" refers to a vector that contains an inserted segment of DNA, the "transgene" that is transcribed into mRNA or replicated as a RNA within a host cell. The phrase "transgene" refers not only to that portion of inserted DNA that is converted into RNA, but also those portions of the vector that are necessary for the transcription or replication of the RNA. A transgene typically comprises a gene-of-interest but needs not necessarily comprise a polynucleotide sequence that contains an open reading frame capable of producing a protein.

As used herein, the phrase "transformed" or "transformation" refers to the introduction of DNA into a cell. The phrases "transformant" or "transgenic" refers to plant cells, plants, and the like that have been transformed or have undergone a transformation procedure. The introduced DNA is usually in the form of a vector containing an inserted piece of DNA.

As used herein, the phrase "transgenic plant" refers to a plant whose genome has been altered by the stable integration of recombinant DNA. A transgenic plant includes a plant regenerated from an originally-transformed plant cell and progeny transgenic plants from later generations or crosses of a transformed plant.

As used herein, the phrase "recombinant DNA" refers to DNA which has been genetically engineered and constructed outside of a cell including DNA containing naturally occurring DNA or cDNA or synthetic DNA.

As used herein, the phrase "selectable marker" or "selectable marker gene" refers to a gene that is optionally used in plant transformation to, for example, protect the plant cells from a selective agent or provide resistance/tolerance to a selective agent. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include gene for neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including Bar (resistance against BASTA® (glufosinate ammonium), or phosphinothricin (PPT)), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. The phrase "marker-positive" refers to plants that have been transformed to include the selectable marker gene.

Various selectable or detectable markers can be incorporated into the chosen expression vector to allow identification and selection of transformed plants, or transformants. Many methods are available to confirm the expression of selection markers in transformed plants, including for example DNA sequencing and PCR (polymerase chain reaction), Southern blotting, RNA blotting, immunological methods for detection of a protein expressed from the vector, e.g., precipitated protein that mediates phosphinothricin resistance, or other proteins such as reporter genes β-glucuronidase (GUS), luciferase, green fluorescent protein (GFP), DsRed, β-galactosidase, chloramphenicol acetyl-transferase (CAT), alkaline phosphatase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate or has been obtained by using genes coding for the mutant target enzymes, 5-enolpyruvylshikimate-3-phosphate synthase (EPSPS). Genes and mutants for EPSPS have been disclosed in U.S. Pat. Nos. 4,940,835, 5,188,642, 5,310,667, 5,633,435, 5,633,448, and 6,566,587, the contents of which are incorporated by reference in their entireties. Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides. Enzymes/genes for glufosinate resistance/tolerance have been disclosed in U.S. Pat. Nos. 5,273,894, 5,276,268, 5,550,318, and 5,561,236, the contents of which are incorporated by reference in their entireties. Enzymes/genes for 2,4-D resistance have been previously disclosed in U.S. Pat. Nos. 6,100,446 and 6,153,401, as well as patent applications US 2009/0093366 (AAD-1) and WO 2007/053482 (AAD-12), the contents of which are hereby incorporated by reference in their entireties. Enzymes/genes for nitrilase have been previously disclosed in U.S. Pat. No. 4,810,648, the content of which is incorporated by reference in its entirety.

Other herbicides can inhibit the growing point or meristem, including imidazolinone or sulfonylurea, and genes for resistance/tolerance of acetohydroxy acid synthase (AHAS) and acetolactate synthase (ALS) for these herbicides have been described. Genes and mutants for AHAS and mutants have been disclosed in U.S. Pat. Nos. 4,761,373, 5,304,732, 5,331,107, 5,853,973, and 5,928,937, the contents of which are incorporated by reference in their entireties. Genes and mutants for ALS have been disclosed in U.S. Pat. Nos. 5,013,659 and 5,141,870, the contents of which are incorporated by reference in their entireties.

Glyphosate resistance genes include mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include glufosinate (phosphinothricin acetyl transferase (PAT) genes from *Streptomyces* species, including *Streptomyces hygroscopicus* and *Streptomyces viridi* chromogenes), and pyridinoxy or phenoxy proprionic acids and cyclohexones (ACCase inhibitor-encoding genes). Herbicide resistance/tolerance genes of acetyl coemzyme A carboxylase (ACCase) have been described in U.S. Pat. Nos. 5,162,602 and 5,498,544, the contents of which are incorporated by reference in their entireties.

A DNA molecule encoding a mutant aroA gene can be obtained under ATCC accession number 39256, and the nucleotide sequence of the mutant gene is disclosed in U.S. Pat. No. 4,769,061 to Comai, European patent application No. 0 333 033 to Kumada et al., and U.S. Pat. No. 4,975,374 to Goodman et al., disclosing nucleotide sequences of glutamine synthetase genes which confer resistance to herbicides such as L-phosphinothricin. The nucleotide sequence of a PAT gene is provided in European application No. 0 242 246 to Leemans et al. Also DeGreef et al., Bio/Technology 7:61 (1989), describes the production of transgenic plants that express chimeric bar genes coding for PAT activity. Exemplary of genes conferring resistance to phenoxy proprionic acids and cyclohexones, including sethoxydim and haloxyfop, are the Acc1-S1, Acc1-S2 and Acc1-S3 genes described by Marshall et al., Theon. Appl. Genet. 83:435 (1992). GAT genes capable of conferring glyphosate resistance are described in WO 2005012515 to Castle et al. Genes conferring resistance to 2,4-D, fop and pyridyloxy auxin herbicides are described in WO 2005107437 and U.S. patent application Ser. No. 11/587,893.

Other herbicides can inhibit photosynthesis, including triazine (psbA and 1s+ genes) or benzonitrile (nitrilase gene). Przibila et al., Plant Cell 3:169 (1991), describes the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

For purposes of the present invention, selectable marker genes include, but are not limited to genes encoding: neomycin phosphotransferase II (Fraley et al. (1986) CRC Critical Reviews in Plant Science, 4:1-25); cyanamide hydratase (Maier-Greiner et al. (1991) Proc. Natl. Acad. Sci. USA, 88:4250-4264); aspartate kinase; dihydrodipicolinate synthase (Perl et al. (1993) Bio/Technology, 11:715-718); tryptophan decarboxylase (Goddijn et al. (1993) Plant Mol. Bio., 22:907-912); dihydrodipicolinate synthase and desensitized aspartade kinase (Perl et al. (1993) Bio/Technology, 11:715-718); bar gene (Toki et al. (1992) Plant Physiol., 100:1503-1507 and Meagher et al. (1996) and Crop Sci., 36:1367); tryptophan decarboxylase (Goddijn et al. (1993) Plant Mol. Biol., 22:907-912); neomycin phosphotransferase (NEO) (Southern et al. (1982) J. Mol. Appl. Gen., 1:327; hygromycin phosphotransferase (HPT or HYG) (Shimizu et al. (1986) Mol. Cell Biol., 6:1074); dihydrofolate reductase (DHFR) (Kwok et al. (1986) PNAS USA 4552); phosphinothricin acetyltransferase (DeBlock et al. (1987) EMBO J., 6:2513); 2,2-dichloropropionic acid dehalogenase (Buchanan-Wollatron et al. (1989) J. Cell. Biochem. 13D:330); acetohydroxyacid synthase (Anderson et al., U.S. Pat. No. 4,761,373; Haughn et al. (1988) Mol. Gen. Genet. 221:266); 5-enolpyruvyl-shikimate-phosphate synthase (aroA) (Comai et al. (1985) Nature 317:741); haloarylnitrilase (Stalker et al., published PCT application WO87/04181); acetyl-coenzyme A carboxylase (Parker et al. (1990) Plant Physiol. 92:1220); dihydropteroate synthase (sul I) (Guerineau et al. (1990) Plant Mol. Biol. 15:127); and 32 kD photosystem II polypeptide (psbA) (Hirschberg et al. (1983) Science, 222:1346).

Also included are genes encoding resistance to: chloramphenicol (Herrera-Estrella et al. (1983) EMBO J., 2:987-992); methotrexate (Herrera-Estrella et al. (1983) Nature, 303:209-213; Meijer et al. (1991) Plant Mol Bio., 16:807-820 (1991); hygromycin (Waldron et al. (1985) Plant Mol. Biol., 5:103-108; Zhijian et al. (1995) Plant Science, 108: 219-227 and Meijer et al. (1991) Plant Mol. Bio. 16:807-820); streptomycin (Jones et al. (1987) Mol. Gen. Genet., 210:86-91); spectinomycin (Bretagne-Sagnard et al. (1996) Transgenic Res., 5:131-137); bleomycin (Hille et al. (1986) Plant Mol. Biol., 7:171-176); sulfonamide (Guerineau et al. (1990) Plant Mol. Bio., 15:127-136); bromoxynil (Stalker et al. (1988) Science, 242:419-423); 2,4-D (Streber et al. (1989) Bio/Technology, 7:811-816); glyphosate (Shaw et al. (1986) Science, 233:478-481); and phosphinothricin (DeBlock et al. (1987) EMBO J., 6:2513-2518). All references recited in the disclosure are hereby incorporated by reference in their entireties unless stated otherwise.

The above list of selectable marker and reporter genes are not meant to be limiting. Any reporter or selectable marker gene are encompassed by the present invention. If necessary, such genes can be sequenced by methods known in the art.

The reporter and selectable marker genes are synthesized for optimal expression in the plant. That is, the coding sequence of the gene has been modified to enhance expression in plants. The synthetic marker gene is designed to be expressed in plants at a higher level resulting in higher transformation efficiency. Methods for synthetic optimization of genes are available in the art. In fact, several genes have been optimized to increase expression of the gene product in plants.

The marker gene sequence can be optimized for expression in a particular plant species or alternatively can be modified for optimal expression in plant families. The plant preferred codons may be determined from the codons of highest frequency in the proteins expressed in the largest amount in the particular plant species of interest. See, for example, EPA 0359472; EPA 0385962; WO 91/16432; Perlak et al. (1991) Proc. Natl. Acad. Sci. USA, 88:3324-3328; and Murray et al. (1989) Nucleic Acids Research, 17: 477-498; U.S. Pat. Nos. 5,380,831; and 5,436,391, herein incorporated by reference. In this manner, the nucleotide sequences can be optimized for expression in any plant. It is recognized that all or any part of the gene sequence may be optimized or synthetic. That is, fully optimized or partially optimized sequences may also be used.

In addition, several transformation strategies utilizing the Agrobacterium-mediated transformation system have been developed. For example, the binary vector strategy is based on a two-plasmid system where T-DNA is in a different plasmid from the rest of the Ti plasmid. In a co-integration strategy, a small portion of the T-DNA is placed in the same vector as the foreign gene, which vector subsequently recombines with the Ti plasmid.

As used herein, the phrase "plant" includes dicotyledons plants and monocotyledons plants. Examples of dicotyledons plants include tobacco, *Arabidopsis*, soybean, tomato, *papaya*, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale.

As used herein, the term "plant" also includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

As used herein, the phrase "plant cell described" or "transformed plant cell" refers to a plant cell that is transformed with stably-integrated, non-natural, recombinant DNA, e.g., by *Agrobacterium*-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g., into a transgenic plant with stably-integrated, non-natural recombinant DNA, or seed or pollen derived from a progeny transgenic plant.

As used herein, the phrase "consensus sequence" refers to an artificial sequence of amino acids in a conserved region of an alignment of amino acid sequences of homologous proteins, e.g., as determined by a CLUSTALW alignment of amino acid sequence of (functional) homolog proteins.

As used herein, the phrase "homolog" refers to a nucleic acid or a protein in a group of proteins that perform the same biological function, e.g., proteins that belong to the same protein family or similar nucleic acids that provide a common enhanced trait in transgenic plants of this invention. Homologs are expressed by homologous genes. With reference to homologous genes, homologs include orthologs, i.e., genes expressed in different species that evolved from common ancestral genes by speciation and encode proteins that retain the same function, but do not include paralogs, i.e., genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog genes have at least 50%, 60%, 70%, 80%, 85%, 90%, 95%, 96%, 97%, 98% or 99% or more sequence identity over the full length of the gene identified as being associated with imparting an enhanced trait when expressed in plant cells. In one aspect of the invention homolog genes have a nucleic acid or amino acid sequence similarity that has at least 85%, 90%, 95%, 96%, 97%, 98% or 99% identity to a consensus sequence of proteins, nucleotides and homologs disclosed herein.

Homologs can be identified by comparison of amino acid sequence, e.g., manually or by use of a computer-based tool using known homology-based search algorithms such as those commonly known and referred to as BLAST, FASTA, and Smith-Waterman. A local sequence alignment program, (e.g., Basic Local Alignment Search Tool (BLAST)) can be used to search a database of sequences to find similar sequences, and the summary Expectation value (E-value) used to measure the sequence base similarity. Because a protein hit with the best E-value for a particular organism may not necessarily be an ortholog, i.e., have the same function, or be the only ortholog, a reciprocal query is used to filter hit sequences with significant E-values for ortholog identification. The reciprocal query entails search of the significant hits against a database of amino acid sequences from the base organism that are similar to the sequence of the query protein. A hit can be identified as an ortholog, when the reciprocal query's best bit is the query protein itself or a protein encoded by a duplicated gene after speciation. A further aspect of the homologs encoded by DNA useful in the transgenic plants of the invention are those proteins that differ from a disclosed protein as the result of deletion or insertion of one or more amino acids in a native sequence.

As used herein, the phrase "percent identity" or "% identity" refers to the extent to which the sequences of DNA or protein segments are invariant throughout a window of alignment of sequences, for example nucleotide sequences or amino acid sequences. An "identity fraction" for a sequence aligned with a reference sequence is the number of identical components which are shared by the sequences, divided by the length of the alignment not including gaps introduced by the alignment algorithm. "Percent identity" is the identity fraction times 100. Percent identity is calculated over the aligned length preferably using a local alignment algorithm, for example BLASTp.

As used herein, the phrase "functional activity" or "functionally active" refers to the proteins/enzymes for use according to the subject invention which have the ability to provide for stress tolerance which can result in an increased yield. Transfer of the functional activity to plant or bacterial systems can involve a nucleic acid sequence, encoding the amino acid sequence for a protein of the subject invention, integrated into a protein expression vector appropriate to the host in which the vector will reside. One way to obtain a nucleic acid sequence encoding a protein with functional activity is to isolate the native genetic material from the bacterial species which produces the protein of interest, using information deduced from the protein's amino acid sequence, as disclosed herein. The native sequences can be optimized for expression in plants. Optimized polynucleotides can also be designed based on the protein sequence.

As used herein, the phrases "control sequences" and "regulatory sequences" are interchangeable and refer to nucleic acid sequences useful for transcription/gene expression in plants. "Control sequences" or "regulatory sequences" may include, but not limited to, promoters, operators, enhancers, origins of replication, ribosome binding sites, termination and polyadenylation signals.

As used herein, the phrase "promoter" refers to regulatory DNA for initializing transcription. A "plant promoter" is a promoter capable of initiating transcription in plant cells whether or not its origin is a plant cell, e.g., is it well known that *Agrobacterium* T-DNA promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, including leaves, roots, or seeds. Such promoters are referred to as "tissue preferred." Promoters that initiate transcription only in certain tissues are referred to as "tissue specific." A "cell type" specific promoter primarily drives expression in certain cell types in one or more organs, for example, vascular cells in roots or leaves. An "inducible" or "repressible" promoter is a promoter which is under environmental or chemical control. Examples of environmental conditions that may affect transcription by inducible promoters include anaerobic conditions, or certain chemicals, or the presence of light. Tissue specific, tissue preferred, cell type specific, and inducible promoters belong to the class of "non-constitutive" promoters. A "constitutive" promoter refers to a promoter which is active under most conditions and in most tissues.

Numerous promoters that are active in plant cells have been previously described. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as disclosed in U.S. Pat. Nos. 5,164,316 and 5,322,938. Useful promoters derived from plant genes are found in U.S. Pat. No. 5,641,876 disclosing a rice actin promoter; U.S. Pat. No. 7,151,204 disclosing a maize chloroplast aldolase promoter and a maize aldolase (FDA) promoter; and U.S. Patent Application Publication 2003/0131377 disclosing a maize nicotianamine synthase promoter. These and numerous other promoters that function in plant cells are known to those skilled in the art and available for use in recombinant polynucleotides described herein to provide for expression of desired genes in transgenic plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see for example U.S. Pat. No. 5,641,876) and rice actin 2 genes, the maize alcohol dehydrogenase gene intron(s), the maize heat shock protein 70 gene intron (see for example U.S. Pat. No. 5,593,874) and the maize shrunken 1 gene intron. See also U.S. Patent Application Publication 2002/0192813A1 disclosing 5', 3' and intron elements useful in the design of effective plant expression vectors.

In some embodiments, sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252), zein Z27 as disclosed by Russell et al. (1997) Transgenic Res. 6(2): 157-166), globulin 1 as disclosed by Belanger et al (1991) Genetics 129:863-872), glutelin 1 as disclosed by Russell (1997, supra), and peroxiredoxin antioxidant (Perl) as disclosed by Stacy et al. (1996) Plant Mol Biol. 31(6):1205-1216.

As used herein, the phrase "operably linked" refers to the association of two or more DNA fragments in a recombinant DNA construct so that the function of one, e.g., protein-encoding DNA, is controlled by the other, e.g., a promoter.

Recombinant DNA constructs are assembled using methods well known to persons of ordinary skill in the art and typically comprise a promoter operably linked to DNA, the expression of which provides the enhanced agronomic trait. Other construct components may include additional regulatory elements, including 5' leaders and introns for enhancing transcription, 3' untranslated regions (for example, polyadenylation signals and sites), and DNA for transit or signal peptides.

Recombinant DNA constructs described herein also generally include a 3' element that typically contains a polyadenylation signal and site. Well-known 3' elements include those from *Agrobacterium tumefaciens* genes such as nos 3', tml 3', tmr 3', tms 3', ocs 3', tr73', for example disclosed in U.S. Pat. No. 6,090,627; 3' elements from plant genes such as wheat (*Triticum aesevitum*) heat shock protein 17 (Hspl 73), a wheat ubiquitin gene, a wheat fructose-1,6-biphosphatase gene, a rice glutelin gene, a rice lactate dehydrogenase gene and a rice beta-tubulin gene, all of which are disclosed in U.S. Patent Application Publication 2002/0192813; and the pea (*Pisum sativum*) ribulose biphosphate carboxylase gene (rbs 3'), and 3' elements from the genes within the host plant.

Constructs and vectors may also include a transit peptide for targeting of a gene to a plant organelle, particularly to a chloroplast, leucoplast or other plastid organelle. For descriptions of the use of chloroplast transit peptides see for example U.S. Pat. Nos. 5,188,642 and 5,728,925.

As used herein, the phrase "expressed" refers to a protein which is expressed or produced in a plant cell when its cognate DNA is transcribed to mRNA that is translated to the protein. As used herein, the phrase "suppressed" refers to decreased expression or activity of a protein. Typically a protein is suppressed in a plant cell when there is a decrease in the amount and/or activity of the protein in the plant cell. The presence or activity of the protein can be decreased by any amount up to and including a total loss of protein expression and/or activity.

As used herein, the phrase "trait" refers to a physiological, morphological, biochemical, or physical characteristic of a plant or particular plant material or cell. In some instances, this characteristic is visible to the human eye, including seed or plant size, or can be measured by biochemical techniques, including detecting the protein, starch, or oil content of seed or leaves, or by observation of a metabolic or physiological process (e.g., by measuring uptake of carbon dioxide), or by the observation of the expression level of a gene or genes (e.g., by employing Northern analysis, RT-PCR, microarray gene expression assays), or reporter gene expression systems, or by agricultural observations including stress tolerance, yield, or pathogen tolerance.

As used herein, the phrase "overexpression" refers to a greater expression level of a gene in a plant, plant cell or plant tissue, compared to expression in a wild-type plant, cell or tissue, at any developmental or temporal stage for the gene. Overexpression can occur when, for example, the genes are under the control of a strong expression signal, including one of the promoters described herein or the cauliflower mosaic virus 35S transcription initiation region known in the art. Overexpression may occur throughout a plant or in specific tissues of the plant, depending on the promoter used.

As used herein, a "nongenic sequence" or "nongenic genomic sequence" is a native DNA sequence found in the nuclear genome of a plant, having a length of at least 1 Kb, and devoid of any open reading frames, gene sequences, or gene regulatory sequences. Furthermore, the nongenic sequence does not comprise any intron sequence (i.e., introns are excluded from the definition of nongenic). The nongenic sequence cannot be transcribed or translated into protein. Many plant genomes contain nongenic regions, where as much as 95% of the genome can be nongenic, and these regions may be comprised of mainly repetitive DNA.

As used herein, a "genic region" is defined as a polynucleotide sequence that comprises an open reading frame encoding an RNA and/or polypeptide. The genic region may also encompass any identifiable adjacent 5' and 3' non-coding nucleotide sequences involved in the regulation of expression of the open reading frame up to about 2 Kb upstream of the coding region and 1 Kb downstream of the coding region, but possibly further upstream or downstream. A genic region further includes any introns that may be present in the genic region. Further, the genic region may comprise a single gene sequence, or multiple gene sequences interspersed with short spans (less than 1 Kb) of nongenic sequences.

As used herein, the term "hypomethylation" or "hypomethylated," in reference to a DNA sequence, defines a reduced state of methylated DNA nucleotide residues in a given sequence of DNA. Typically, the decreased methylation relates to the number of methylated adenine or cytosine residues, relative to the average level of methylation found in nongenic sequences present in the genome of a plant for example soybean or maize.

The term "in proximal location to a genic region" when used in reference to a nongenic sequence defines the relative location of the nongenic sequence to a genic region. Specifically, the number of genic regions within a 40 Kb neighborhood (i.e., within 40 Kb on either end of the selected optimal soybean genomic loci sequence) is analyzed. The number of genic regions may range from a minimum of 1 gene to a maximum of 18 genes within the 40 Kb neighborhood.

The term "evidence of recombination" as used herein relates to the meiotic recombination frequencies between any pair of genomic markers across a chromosome region comprising the selected sequence. The recombination frequencies were calculated based on the ratio of the genetic distance between markers (in centimorgan (cM)) to the physical distance between the markers (in megabases (Mb)). For a selected sequence to have evidence of recombination, the selected sequence must contain at least one recombination event between two markers flanking the selected sequence as detected using a high resolution marker dataset generated from multiple mapping populations.

As used herein the term "relative location value" is a calculated value defining the distance of a genomic locus from its corresponding chromosomal centromere. For each selected sequence, the genomic distance from the native location of the selected sequence to the centromere of the chromosome that it is located on, is measured (in Bp). The relative location of selected sequence within the chromosome is represented as the ratio of its genomic distance to the centromere relative to the length of the specific chromosomal arm (measured in Bp) that it lies on. These relative location values for the optimal nongenic genomic loci can be generated for different plants, the relative location values for the dataset may range from a minimum of 0 to a maximum of 0.99682 ratio of genomic distance.

The term "exogenous DNA sequence" as used herein is any nucleic acid sequence that has been removed from its native location and inserted into a new location altering the sequences that flank the nucleic acid sequence that has been moved. For example, an exogenous DNA sequence may comprise a sequence from another species.

"Recombination" refers to a process of exchange of genetic information between two polynucleotides, including but not limited to, donor capture by non-homologous end joining (NHEJ) and homologous recombination. As used herein, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the nucleotide sequence that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide. For HR-directed integration, the donor molecule contains at least 2 regions of homology to the genome ("homology arms") of least 50-100 base pairs in length. See, e.g., U.S. Patent Publication No. 20110281361, the content of which is hereby incorporated by reference.

As used herein, the phrase "gene expression" refers to the conversion of the information, contained in a gene, into a gene product. A gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "substantially homologous" or "substantial homology," with regard to a contiguous nucleic acid sequence, refers to contiguous nucleotide sequences that hybridize under stringent conditions to the reference nucleic acid sequence. For example, nucleic acid sequences that are substantially homologous to a reference nucleic acid sequence are those nucleic acid sequences that hybridize under stringent conditions (e.g., the Moderate Stringency conditions set forth, supra) to the reference nucleic acid sequence. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

In some instances "homologous" may be used to refer to the relationship of a first gene to a second gene by descent from a common ancestral DNA sequence. In such instances, the term, homolog, indicates a relationship between genes separated by the event of speciation (see ortholog) or to the relationship between genes separated by the event of genetic duplication (see paralog). In other instances "homologous" may be used to refer to the level of sequence identity between one or more polynucleotide sequences, in such instances the one or more polynucleotide sequences do not necessarily descend from a common ancestral DNA sequence. Those with skill in the art are aware of the interchangeably of the term "homologous" and appreciate the proper application of the term.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

According to the methods and/or systems provided herein, database and/or map data can be used for assessment or prediction of transgene performance and/or stability by profiling the local chromatin state, in particular the abundance of H3K9me2, in the vicinity of the transgene-inserted locus. As provided here, a threshold value can be assigned to predict the potential risk of transgene silencing for transgenic integration occurring with highly H3K9me2 enriched genomic regions. To assess the local chromatin structure, a genome-wide histone3 lysine (K) 9 di-methylation (H3K9me2) map in soybean (*Glycine max*) cv Maverick is constructed. H3K9me2 are often observed within the silenced heterochromatic regions including centromere and telomere-carrying repetitive sequences. This genome-wide H3K9me2 map allows us to predict the chromatin structure (opened or packed) in any locus within the soybean genome and provides an assessment on potential for silencing.

Shoot and root tissues of soybean (*Glycine max*) cv Maverick are harvested at v1 (~12 days after planting) stage, and then cross-linked using 1% formaldehyde. The cross-linked tissues is used for the chromatin immunoprecipitation (ChIP) assay using H3K9me2 antibody (Millipore 17-648) where normal Rabbit IgG (Millipore Cat. 12-370) is used as a negative control. Three independent ChIP assays from each tissue are performed and the ChIPed DNA is prepared for sequencing using HiSeq. The sequencing reads are listed in Table 1.

TABLE 1

ChIP-seq reads from HiSeq

| Sample Name | Label | Species | Bar-code | Total Read # | Mapped Read # | Mapping Ratio |
|---|---|---|---|---|---|---|
| x486_7 | Shoot-1 (1) | Soybean (Gmax_109) | Index 5 | 76,305,548 | 57,296,302 | 75.09% |
| x486_8 | Shoot-2 (2) | Soybean (Gmax_109) | Index 6 | 98,536,615 | 78,863,536 | 80.03% |
| x486_9 | Shoot-2 (3) | Soybean (Gmax_109) | Index 12 | 90,263,804 | 74,632,245 | 82.68% |
| x486_10 | Root-3(1) | Soybean (Gmax_109) | Index 4 | 91,350,018 | 68,443,285 | 74.92% |
| x486_11 | Root-3(2) | Soybean (Gmax_109) | Index 12 | 99,169,687 | 74,526,487 | 75.15% |
| x486_12 | Root-4(3) | Soybean (Gmax_109) | Index 6 | 92,090,396 | 69,694,991 | 75.68% |

ChIP-Seq data analysis—Raw sequencing data from the H3K9me2 ChIP-seq experiments are aligned using Bowtie to the *Glycine Max* Williams82 genome. The MACS (model-based analysis of ChIP-seq) peak finding algorithm can be used to identify regions of H3K9me2 enrichment over background, where a "peak" represents a genomic stretch that is predicted to be enriched for H3K9me2 as compared to its genomic neighborhood. On the other hand, a "summit" represents the genomic location that has the greatest enrichment within a predicted "peak."

According to this example, ChIP-seq data is consistent among technical replicates. To reduce the variation and noise resulted from the ChIP-seq data, three technical replicates of ChIP-seq are performed individually. To examine if the ChIP pull-downs from each round are consistent and reflect the genuine H3K9me2 modification in the soybean genome, the pull-down from each technical rep can be compared. Among the three technical replicates, the ChIP-seq data is consistent to each other, indicating that the pull-downs are consistent from each round of ChIP experiment. Therefore, that the CHIP-seq protocols used in this example are highly replicable across root and shoot technical replicate samples.

Example 2

H3K9me2 enrichment is associated with heterochromatic regions and gene silencing—H3K9me2 is associated with heterochromatin (tightly packed chromatin structure) and one of the highly conserved histone marks accounting for transcriptional repression in eukaryotes. To determine whether H3K9me2 is associated with heterochromatic region and gene silencing in soybean, the enrichment of H3K9me2 within the genic region (measured as the number of H3K9me2 "peaks" predicted within a genic region—higher peak number represents greater extent of H3K9H3K9me2 enrichment) is investigated and compared with the corresponding gene expression level (measured using RNAseq technology, in units of normalized read counts). Herein, we observed that the genic regions with zero or one peak of H3K9me2 show a significant range of gene expression. On the other hand, the genic regions with more than two peaks of H3K9me2 are associated relatively lower levels of gene expression. This indicates that higher enrichment of H3K9me2 is highly associated with the lower levels of gene expression in soybean.

In addition to understanding H3K9me2 content in genic regions, we further identify higher levels of H3K9me2 in transposable elements which are often associated with highly repetitive and transcriptionally repressed regions within the genome. We compare the distribution of H3K9me2 enrichment between transposable elements and genes in soybean genome. On average, the H3K9me2 enrichment of the majority of transposon elements is much higher than regular genes. This data further demonstrates that the enrichment of H3K9me2 is highly associated with the repressive status of soybean genome.

Figure 1:
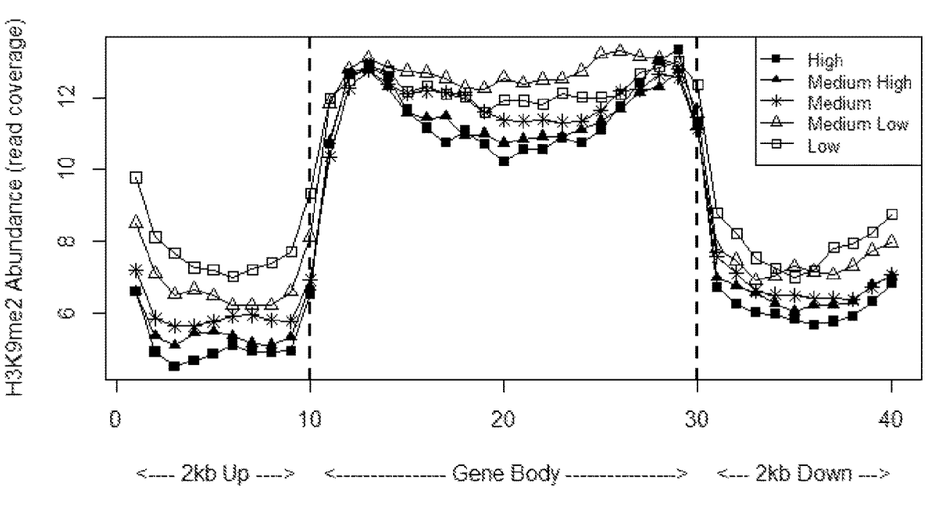
FIG. 1 shows H3K9me2 abundance within Soybean gene features (gene body, 2 kb upstream, 1 kb downstream) as a function of different expression categories (High, Medium High, Medium, Medium low, Low).

To build on our understanding of how H3K9me2 abundance is associated with gene expression, we categorize genes based on their expression levels into five different expression categories—High, Medium High, Medium, Medium Low, and Low—and then selected a representative number of 500 genes from each category (see FIG. 1). For each gene within each category, the H3K9me2 abundance across the genic region was calculated. The genic region is then divided into three sections—gene body, 2 kb upstream, and 1 kb downstream. An average value for H3K9me2 abundance within each section is plotted for each expression category in FIG. 1. High and Medium high expression categories can be distinguished from Low and Medium Low expression categories based on their H3K9me2 abundance within all three genic sections. This provides a unique view and a statistical model for how H3K9me2 data can be used to predict the expression level for a particular transgene of interest. Together, the data above indicated that H3K9me2 is a conserved repressive histone mark in soybean as well and the abundance of H3K9me2 is associated with heterochromatic region and transcriptional repression in soybean. We conclude a threshold is link to acceptable expression levels where the genic region has one peak of H3K9me2 profiling data mapped to soybean genomes. According to this example, a databased for the soybean genome is established based on the H3K9me2 profiling data.

Example 3

Assessment of the H3K9me2 enrichment using the soybean lead events to validate the prediction of expression levels based on the H3K9me2 profiling data. To evaluate the practical use of applying H3K9me2 map as a tool to assess the potential risk of transgene silencing, nine soybean lead events from Enlist and Insect Resistance constructs are selected and listed in Table 2. Because the insertion sites of these lead events are already known, the H3K9me2 enrichment profiles in the vicinity (5 kb) of transgene-inserted site are evaluated to predict the risk of gene silencing. Because all the lead events are selected based on stable transgene expression and stability, it is expect that the transgene is inserted in a locus with low H3K9me2 enrichment (peak no. ≤1). In the 5 kb window of the transgene-inserted site among nine distinct events, six events showed zero peak and three events show one peak of H3K9me2. The low H3K9me2 enrichment is corresponding to the stable transgene expression. This indicates that H3K9me2 profiling provides an effective tool to predict the risk of gene silencing.

TABLE 2

Enrichment of H3K9me2 in the 5kb vicinity of transgene-inserted site of the commercial soybean events

| Soybean events | Chromosome | Start | Stop |
|---|---|---|---|
| pDAB4468.04.16.1 | Gm 04 | 46004353 | 46004354 |
| pDAB4464.11.04.1 | Gm 15 | 876318 | 876319 |
| pDAB4472.16.06.1 | Gm 08 | 8345349 | 8345350 |
| pDAB9582.812.09.1 | Gm 05 | 2810964 | 2810965 |
| pDAB9582.814.19.1 | Gm 02 | 10027415 | 10027416 |
| pDAB9582.146.06.1 | Gm 17 | 7737798 | 7737799 |
| pDAB9582.140.11.1 | Gm 18 | 57058706 | 57058707 |
| pDAB9582.816.15.1 | Gm 03 | 46300211 | 46300212 |
| pDAB9582.816.12.1 | Gm 04 | 48406612 | 48406613 |

We claim:

1. A method for predicting the risk of transgene silencing, comprising,
   (a) generating histone methylation/acetylation profile data of a plant's genome from a physical assay;
   (b) assembling the histone methylation/acetylation profile data of step (a) into a histone methylation/acetylation database showing peak numbers of the histone methylation/acetylation profiles;
   (c) analyzing sequences of at least one transgene insertion site from a transgenic event;
   (d) comparing the sequences of the transgene insertion site of step (c) with the histone methylation/acetylation database of step (b); wherein
      (i) if the transgene insertion site falls into peak zero or peak one of the histone methylation/acetylation profiles, there is no risk of transgene silencing, or
      (ii) if the transgene insertion site falls into peak two or more of the histone methylation/acetylation profiles, there is significant risk of transgene silencing;
   (e) selecting the transgenic event with a lower probability of transgene silencing; and
   (f) obtaining a plant that comprises the selected transgenic event.

2. The method of claim 1, wherein the histone methylation/acetylation profile data is generated using a chromatin immunoprecipitation sequencing (ChIP-seq) assay.

3. The method of claim 1, wherein the histone methylation/acetylation profile data is associated with histone methylation/acetylation selected from the group consisting of H3K4me2, H3K4me3, H3K9/14ac, H3K9me2, H3K9me3, H3K27me1, H3K27me3 and H4K20me3, and combinations thereof.

4. The method of claim 1, wherein the histone methylation/acetylation profile data is associated with histone methylation/acetylation selected from the group consisting of H3K9me2, H3K9me3, H3K27me1, H3K27me3 and H4K20me3, and combinations thereof.

5. The method of claim 1, wherein the histone methylation/acetylation profile data is associated with H3K9me2 methylation.

6. The method of claim 1, wherein the plant is selected from soybean, maize, canola, cotton, wheat, and rice.

7. The method of claim 1, wherein the sequences of the transgene insertion site are obtained by direct sequencing.

* * * * *